(12) United States Patent
Marquardt et al.

(10) Patent No.: US 8,078,410 B2
(45) Date of Patent: Dec. 13, 2011

(54) SENSING USING POLARIZATION DIVERSITY AND WAVELENGTH DEPENDENT BACKSCATTER

(75) Inventors: John H. Marquardt, Berthoud, CO (US); Tahllee Baynard, Lafayette, CO (US)

(73) Assignee: Lockheed Martin Coherent Technologies, Inc., Louisville, CO (US)

( * ) Notice: Subject to any disclaimer, the term of this patent is extended or adjusted under 35 U.S.C. 154(b) by 489 days.

(21) Appl. No.: 12/263,404

(22) Filed: Oct. 31, 2008

(65) Prior Publication Data
US 2010/0280765 A1    Nov. 4, 2010

Related U.S. Application Data

(60) Provisional application No. 60/984,696, filed on Nov. 1, 2007.

(51) Int. Cl.
*G01N 31/00* (2006.01)
(52) U.S. Cl. ............... 702/28; 702/22; 702/23; 702/24; 702/29; 702/30; 356/364
(58) Field of Classification Search ............... 702/24, 702/28, 30
See application file for complete search history.

(56) References Cited

U.S. PATENT DOCUMENTS

| | | | |
|---|---|---|---|
| 5,049,738 A * | 9/1991 | Gergely et al. | 250/301 |
| 7,129,095 B2 | 10/2006 | Boehr et al. | |
| 7,768,643 B1 * | 8/2010 | Janssens et al. | 356/369 |
| 2003/0191610 A1 | 10/2003 | Chen et al. | |
| 2004/0185438 A1 * | 9/2004 | Ecker | 435/5 |
| 2006/0249683 A1 * | 11/2006 | Goldberg et al. | 250/370.01 |
| 2007/0024849 A1 | 2/2007 | Carrig et al. | |

OTHER PUBLICATIONS

Jeys, et al., "Advanced Trigger Development," 2007, Lincoln Laboratory Journal, vol. 17, No. 1, pp. 29-62, Nov. 1, 2007.
Marquardt, et al., "Measurement of Bio-Aerosols With a Polarization-Sensitive, Coherent Doppler Lidar," Proc. 5th Joint Conference on Standoff Detection for Chemical and Biological Defense, Williamsberg, VA, Sep. 24-28, 2001, pp. 1-11.
Theriault, et al., "Passive Standoff Detection of BG Aerosol: Method and Field Trial Results," Chemical and Biological Standoff Detection, Proc. of SPIE, pp. 163-172, vol. 5268, 2004, Chemical and Biological Standoff Detection.
Eugene Hecht, "Optics," Ch. 8, Polarization, Addison Wesley, pp. 308-365, 2001.
Grant, "Lidar for Atmospheric and Hydrospheric Studies," Tunable Laser Applications, F. J. Duarte ed., Marcel Dekker, pp. 213-305, 1995.

(Continued)

*Primary Examiner* — Drew A Dunn
*Assistant Examiner* — Mischita Henson
(74) *Attorney, Agent, or Firm* — McDermott Will & Emery LLP

(57) ABSTRACT

Provided herein are systems and methods capable of detecting and discriminating and/or classifying hazardous biological agents or other hazardous agents. In one aspect, a system measures electromagnetic energy scattered by a material at the different polarizations states and wavelengths. The system then combines the measured electromagnetic wavelengths at the different polarization states and wavelengths into different combinations to produce input parameters for a classifier. The input parameters include both depolarization and wavelength-dependent elastic backscatter measurements of the material illuminated by transmitted electromagnetic energy. The combination of wavelength dependent depolarization measurements and wavelength dependent backscatter measurements provides a unique capability to classify (or discriminate) based on size, shape, and refractive index. The combined measurements provided in the input parameters increases the information available to the classifier to classify materials, enabling the classifier to classify a wider range of materials.

42 Claims, 9 Drawing Sheets

OTHER PUBLICATIONS

Gurton, et al. "Measured Infrared Spectral Extinction for Aerosolized *Bacillus subtilis* Var. *niger* Endospores From 3 to 13 μm," *Applied Optics*, pp. 4443-4448, vol. 40, No. 25, Sep. 1, 2001.

Zakel, et al., "High-Brightness Rapidly-Tunable Cr:ZnSe Lasers," 20th Anniversary Meeting Advanced Solid-State Photonics, pp. 723-727, Feb. 6-9, 2005, Vienna.

* cited by examiner

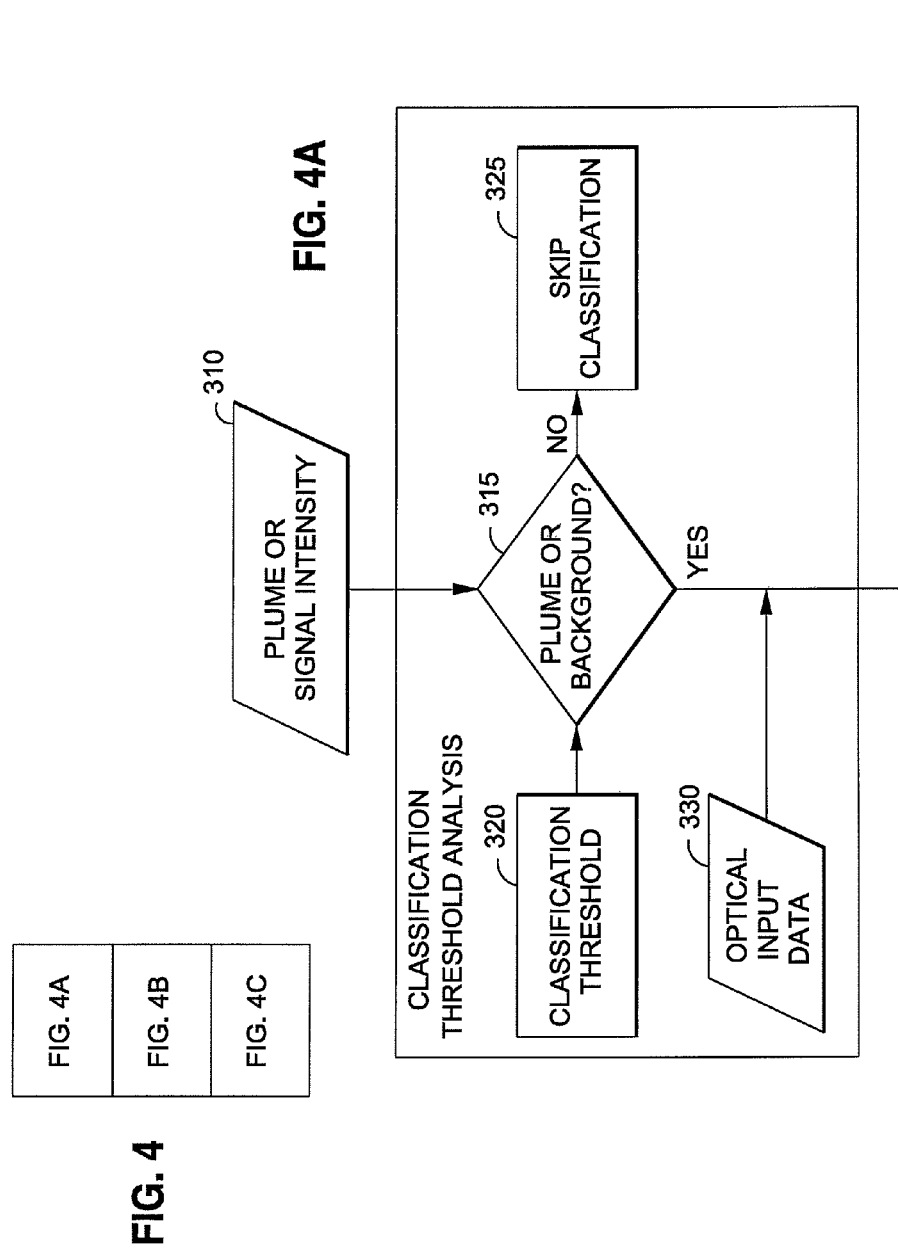

SENSING USING POLARIZATION DIVERSITY AND WAVELENGTH DEPENDENT BACKSCATTER

RELATED APPLICATION

The present application claims the benefit of priority under 35 U.S.C. §119 from U.S. Provisional Patent Application Ser. No. 60/984,696, entitled "Airborne Biological Agent Detection," filed on Nov. 1, 2007, which is hereby incorporated by reference in its entirety for all purposes.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W911 SR-06-C-0019 awarded by the Polarization-Se Multispectral ("P-SM").

FIELD

The present invention relates generally to systems and methods for sensing, and more particularly to systems and methods for detection and discrimination and/or classification of species distributed in the atmosphere, such as biological species.

BACKGROUND

Light Detection and Ranging (lidar) systems are used in numerous areas of practical interest to make remote measurements. In lidar systems, a light beam is sent to a target and a detection system is used to extract information about the target.

Heightened concerns in recent years about potential use of airborne chemical and biological agents to cause harm has increased the urgency of finding methods to remotely detect and locate such agents. It has generally been found difficult to use remote sensing methods to a) detect threat species and b) reliably discriminate the threat species from other species that may also be present or classify the threat species. In the case of biological agents like anthrax it is in principle possible to detect their presence by simply collecting scattered light from the particles. However, simple light scattering measurements often cannot tell the difference between types of aerosols. For example, the scattered light "signature" of an anthrax particle is similar to the scattered light signature of common dust.

To enhance stand-off biological agent discrimination and/or classification, other laser based remote sensing techniques have been developed, in particular Laser Induced Fluorescence or LIF. In LIF, a short wavelength (typically in the UV or visible spectral range) laser illuminates the particles, the light is absorbed and subsequently re-emitted at a different (longer) wavelength. By detecting the longer wavelength emission one may infer that a biological aerosol is present (since inorganic materials tend not to fluoresce). However, there is frequently little in the fluorescence signature that permits one to distinguish one biological species from another.

Polarization and wavelength normalized depolarization ratio lidars have been used to discriminate stratospheric ice from water and *bacillus globigii* (Bg) from dust, pollens, and smokes, respectively. Discrimination based on depolarization measurements is primarily dependent on the degree of non-sphericity of particles. However, as the types of biological aerosol species expand, and the various methods of biological species preparation and dissemination methods are assessed, more robust measurement techniques are needed.

What is needed are systems and methods capable of detecting and discriminating and/or classifying hazardous biological agents to enable suitable action to taken when a threat species is found. In addition, systems and methods should desirably permit detection at several kilometers. In addition, systems and methods should be capable of day or night operation and be operationally eye-safe.

SUMMARY

Provided herein are systems and methods capable of detecting and discriminating and/or classifying hazardous biological agents or other hazardous agents.

In one aspect, a system transmits electromagnetic energy (e.g., optical beam) at two or more different wavelengths and a polarization state toward an area of interest. A material illuminated by the transmitted electromagnetic scatters the electromagnetic energy back toward the system. The system receives the scattered electromagnetic energy and measures the power of the received scattered electromagnetic energy at two or more polarization states and two or more wavelengths. The system then combines the measured electromagnetic energy at the different polarizations states and wavelengths into different combinations to produce input parameters for a classifier. The input parameters include both depolarization and wavelength-dependent back scattering measurements of the material illuminated by transmitted electromagnetic energy. The depolarization measurement provides information on the shape and absorption features of the material and the wavelength-dependent information provides information on the shape and index of refraction of the material. The combined measurements provided in the input parameters increases the information available to the classifier to classify materials, enabling the classifier to classify a wider range of materials.

In one aspect, the classifier may implement a discriminator that broadly classifies a material as either a threat or a non-threat. In another aspect, the classifier may classify a material to a specific type of hazardous material.

It is to be understood that both the foregoing summary of the invention and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

DETAILED DESCRIPTION

Figure 1:
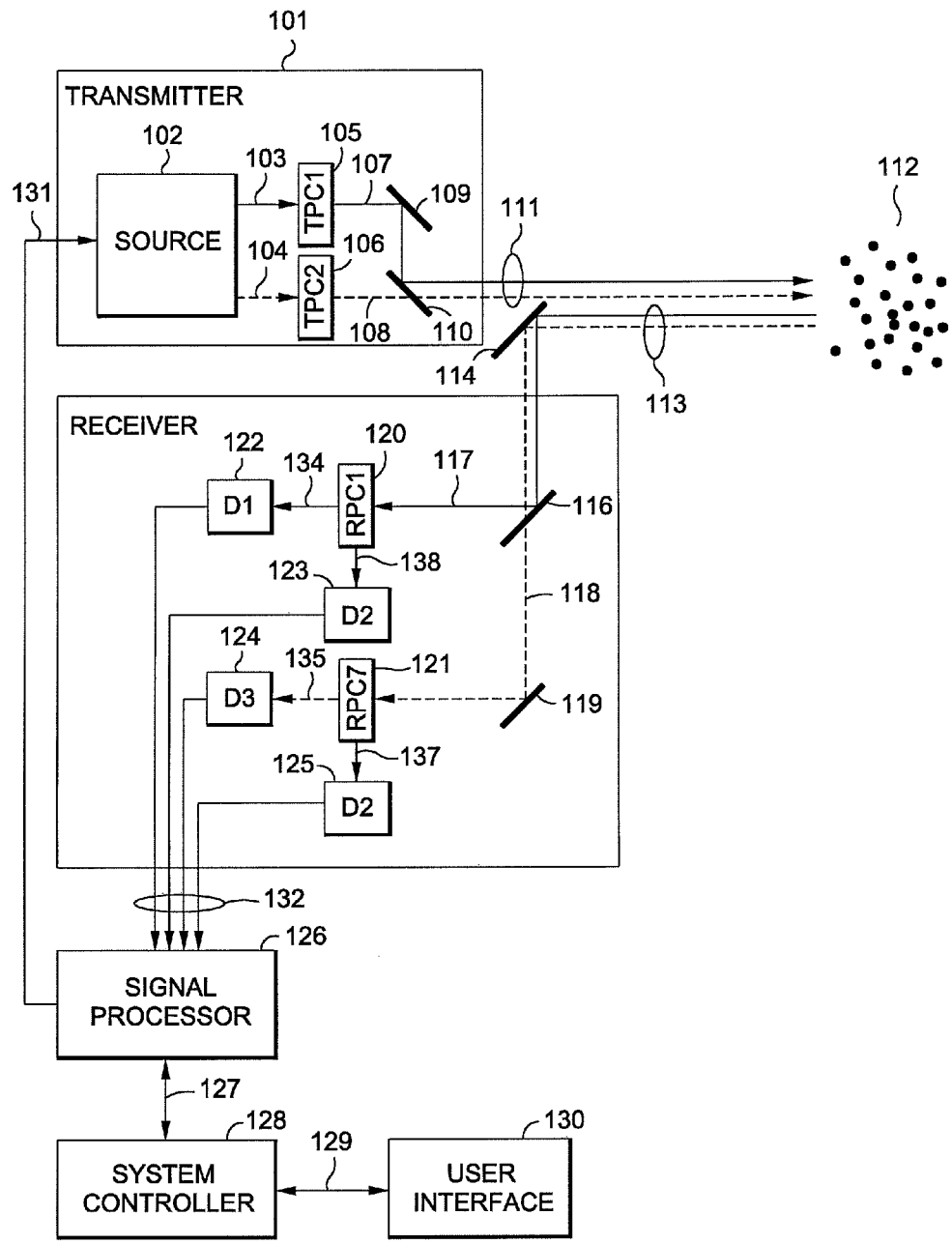
FIG. 1 illustrates a lidar system according to an aspect of the disclosure.

In the following detailed description, numerous specific details are set forth to provide a full understanding of the present invention. It will be obvious, however, to one ordinarily skilled in the art that the present invention may be practiced without some of these specific details. In other instances, well-known structures and techniques have not been shown in detail to avoid obscuring concepts of the present invention.

Reference will now be made in detail to aspects of the subject technology, examples of which are illustrated in the accompanying drawings, wherein like reference numerals refer to like elements throughout.

Polarization and Light Scattering by Small Particles

Polarization is the property of light that describes the orientation of the electric field vector perpendicular to the propagation axis of a light beam as discussed, for example, in the text *Optics* by Eugene Hecht, Addison Wesley 2001, hereby incorporated by reference. The photons that make up a light beam have either a right-hand or left-hand circular polarization state, meaning that the polarization vector rotates clockwise or counter-clockwise about the propagation axis. All other polarization states that may describe a light beam result from a linear combination of these states. For example, horizontal (h) and vertical (v) linear states result from equal amounts of right-hand and left-hand light with the proper phase relationships between the circular states. Two polarization states are said to be orthogonal if the product of the polarization vectors is zero, as is the case for the two circular states and the two linear states. It is well known that interaction of photons with materials frequently alters the polarization state such that light prepared in a given polarization state that is backscattered from small particles, may show a different polarization state than was incident. An example of this is the scattering of light from ice particles in Cirrus clouds, as discussed, for example, by Grant in "*Lidar for Atmospheric and Hydrospheric Studies*", in Tunable Laser Applications, F. J. Duarte ed., Marcel Dekker 1995, hereby incorporated by reference. The combination of this alteration of a polarization state as a result of an interaction with the material and the spectral reflectivity of the material can be used to discriminate and/or classify different materials. As used herein the word "discriminate" means to broadly classify such as classifying whether a particle is biological in nature as opposed to non-biological material, or whether an aerosol is hazardous or benign. Discriminating does not require specific identification of the particle.

In the most general terms an incident polarization state can be uniquely described by a Stokes vector u and the effect of the material on the polarization can be described by a Mueller matrix M, so that the Stokes vector of the scattered light is described by vector u' according to the relationship u'=M·u. The Mueller matrix itself is dependent on the material, and in the case of small particles is highly dependent on the microscopic structure of the particles. For this application co-located transmitter and receiver are used so signatures are based on the backscatter parameter defined at 180 or near to 180 degrees. The components of the Mueller matrix for well behaved randomly oriented scatters can be described by Equation 1. Efficient selection of polarization dependent measurements allows one to estimate the entire matrix and capture the scattering properties of the target.

$$F(\lambda) = \begin{bmatrix} a_1 & 0 & 0 & 0 \\ 0 & a_2 & 0 & 0 \\ 0 & 0 & -a_2 & 0 \\ 0 & 0 & 0 & a_1 - 2a_2 \end{bmatrix} \quad (1)$$

Discrimination and/or classification is based on optical inputs associated with the parameters: $a_1(\lambda_1)$, $a_2(\lambda_1)$, $a_1(\lambda_2)$, $a_2(\lambda_2)$, $a_1(\lambda_3)$, etc. These terms can be calculated or the algorithm can be based on raw inputs that would be used to derive the basic components of the Mueller matrix elements. A signature based on these components can be realized through multiple combinations as shown below:

$$C_1 = \frac{a_1(\lambda_1)}{a_1(\lambda_1) + a_1(\lambda_2) + a_1(\lambda_3)} \quad (2)$$

$$C_2 = \frac{a_1(\lambda_2)}{a_1(\lambda_1) + a_1(\lambda_2) + a_1(\lambda_3)}$$

$$C_3 = \frac{a_1(\lambda_3)}{a_1(\lambda_1) + a_1(\lambda_2) + a_1(\lambda_3)}$$

$$C_4 = \frac{a_2(\lambda_1)}{a_1(\lambda_1) + a_1(\lambda_2) + a_1(\lambda_3)}$$

$$C_5 = \frac{a_2(\lambda_2)}{a_1(\lambda_1) + a_1(\lambda_2) + a_1(\lambda_3)}$$

$$C_6 = \frac{a_2(\lambda_3)}{a_1(\lambda_1) + a_1(\lambda_2) + a_1(\lambda_3)}$$

where $C_i$ is an optical input parameter for a classification algorithm. The resulting signature can also be realized through the backscatter coefficient and the partitioning of polarization states of the return energy as described as follows:

$$C_1 = \frac{P_i(\lambda_1)}{P_i(\lambda_1) + P_j(\lambda_1) + P_i(\lambda_2) + P_j(\lambda_2) + P_i(\lambda_3) + P_j(\lambda_3)} \quad (3)$$

$$C_2 = \frac{P_j(\lambda_1)}{P_i(\lambda_1) + P_j(\lambda_1) + P_i(\lambda_2) + P_j(\lambda_2) + P_i(\lambda_3) + P_j(\lambda_3)}$$

$$C_3 = \frac{P_i(\lambda_2)}{P_i(\lambda_1) + P_j(\lambda_1) + P_i(\lambda_2) + P_j(\lambda_2) + P_i(\lambda_3) + P_j(\lambda_3)}$$

$$C_4 = \frac{P_j(\lambda_2)}{P_i(\lambda_1) + P_j(\lambda_1) + P_i(\lambda_2) + P_j(\lambda_2) + P_i(\lambda_3) + P_j(\lambda_3)}$$

$$C_5 = \frac{P_i(\lambda_3)}{P_i(\lambda_1) + P_j(\lambda_1) + P_i(\lambda_2) + P_j(\lambda_2) + P_i(\lambda_3) + P_j(\lambda_3)}$$

$$C_6 = \frac{P_j(\lambda_3)}{P_i(\lambda_1) + P_j(\lambda_1) + P_i(\lambda_2) + P_j(\lambda_2) + P_i(\lambda_3) + P_j(\lambda_3)}$$

where $P_j$ represents the scattered power measured in the same polarization state as the transmitted beam and $P_i$ represents the scattered power in an orthogonal polarization state after the total return intensity is partitioned into the appropriate polarization components at the receiver. The combinations of different polarization states and wavelengths of the scattered power shown in Eq. (3) are exemplary only, and other combinations may be used. Two or more polarization states and two or more different wavelengths may be used.

The different polarization states of the scattered power measured at the receiver can be used to measure the depolarization of a particle. The depolarization measurement provides information on the shape and absorption features of the particle. In addition, the scattered power at different wavelengths measured at the receiver can be used to measure the wavelength-dependent back scattering of a particle. The wavelength dependent back scattering measurement provides information on the size and index of refraction of the particle.

The different polarizations and wavelengths of the scattered power measured at the receiver can be combined into different combinations (e.g., based on Eq. (3)) to measure both depolarization and wave-length dependent back scattering. Thus, the different combinations capture the information of both types of measurements including the shape, absorption features, size and refractive index of a particle. Combining the two measurements increases the amount of information available for discrimination and/or classification. This additional information enables a discriminator and/or classifier to discriminate and/or classify a greater number of threat categories.

Generalized System Architecture

A system for obtaining optical measurements for discrimination and/or classification is shown in FIG. 1. The system comprises a transmitter subsystem 101 for transmitting light at two wavelengths in a well-defined polarization state, a receiver subsystem 115 for measuring the depolarization of the scattered light at both wavelengths, and a signal processor 126 for computing optical input parameters which are inputted to a discrimination and/or classification algorithm. The optical input parameters may include combinations of the measured scattered light at the different polarization states and different wavelengths to capture both depolarization and wavelength-dependent backscattering information.

To accomplish this the system incorporates a source 102 that outputs two light beams 103 and 104 at different wavelengths. Beams 103 and 104 are passed through transmit polarization controllers (TPC) 105 and 106 that ensure that beams 107 and 108 have the desired polarization states. These TPCs may be absent if the beams 103 and 104 already have desired polarization states, for example linear, but generally comprise polarizers and/or optical retarders to produce the desired states. Beams 107 and 108 are next combined using optics 109 and 110 such that the two beams overlap spatially and in propagation angle, effectively forming one beam 111 (for clarity shown in FIG. 1 as two spatially separated lines). Depending upon the measurement scenario it is not strictly necessary to combine the beams into a single overlapping beam, but it is frequently desired to ensure that all wavelength beams interact with the same scattering centers. The combination optics may comprise, as examples, dichroic coatings or diffraction gratings. The combined beam 111 is transmitted to scattering centers 112 where the light interacts with the scatterers to produce scattered light 113 propagating towards the receiver 115. Again light at the two wavelengths is illustrated in FIG. 1 as two separated lines for clarity, but generally the scattered light at the two wavelengths overlaps spatially. The light is directed into the receiver 115 using mirror 114 and is directed to a wavelength separating optic 116. This optic, which may again be a dichroic coated substrate or a diffraction grating, separates the two wavelengths into beam 117 at one wavelength and beam 118 at the other wavelength.

Beam 118 is next redirected using mirror 119 and both beams 117 and 118 are passed through receive polarization controllers (RPC) 120 and 121, respectively, before being detected at detectors 122 through 125. The RPCs act as polarization analyzers that transmit the fraction of light present in one predetermined polarization state as beams 134 and 135 for detection at detectors 122 and 124, while reflecting the orthogonal polarization state as beams 136 and 137 for detection at detectors 123 and 125. In a simple case where the desire is to separate the receive beams into linear polarization states the RPCs 120 and 121 may be linear polarizers. In other cases the RPCs may contain a combination of fractional waveplates and polarizers to perform the action of separating the received light into two orthogonal polarization states for detection. In cases where measurements at different polarization states are carried out sequentially the RPCs are set to transmit a first polarization state and then switched to transmit an orthogonal state. In such cases only two detectors are required. In this example the returned light is first separated by wavelength and then by polarization state. Alternatively the light could be first separated by polarization state and then by wavelength.

The light detected by detectors 122-125 is converted into signals 132 that are captured by signal processor 126. In the case of using four detectors all four signals 132 are captured by the processor 126, which may subsequently calculate optical inputs for a discrimination and/or classification algorithm. In case of using two detectors and changing receive polarization states between detection events, data is collected for one polarization state, followed by a change in the analyzer settings and collection of data at the orthogonal polarization state. The signal processor 126 then calculates the optical inputs from the two data sets.

The processed data is output as a signal 127 to a system controller 128 that normally also outputs a signal 129 to a user interface 130 that may be a display, a data storage device, an alarm, or any other suitable device. System controller 128 normally also carries out additional functions that are practically useful but not essential to the operating principle of the invention. Such functions may include control of the transmit source via a connection 131, communications and/or control of the signal processor via 127, as well as control of the transmit and receive polarization controllers in cases where these are not fixed. In a common situation the system as described would be used in conjunction with a scanning system that permits pointing the transmit beam over an angular range to scan a volume of space in search of specific species of interest. It is also stressed that operational systems frequently do not need all elements shown in FIG. 1. For example, if laser or non-linear frequency converted laser beams are used as the lights source it is common that the light beams are linearly polarized. In cases where illumination with a linearly polarized beam is suitable the TPCs 105/106 would not be required. In such a case the receiver would require only simple polarizers as RPCs in order so detect linear polarization states.

In the context of light sources it is noted that both continuous-wave (CW) and pulsed devices can be used, provided only that a suitable source is available. Under some circumstances pulsed sources are preferred. One such circumstance is when the interrogated volume of interest is between the source and a reflecting surface, such as the ground. If a CW source is used the receiver may pick up scattered light from the reflecting surface whose magnitude far exceeds the signals from the particles of interest, thereby making the measurements difficult or impossible. A pulsed source having a pulse duration of, for example, 0.1-1000 ns permits one to time resolve and hence range resolve the scattered signals so that light from the particles arrives back at the receiver before a potentially much bigger signal arrives from the background. A second advantage of pulsed sources is that it is frequently convenient to generate the desired operating frequency by converting light from a fixed frequency laser using an optical parametric oscillator (OPO) or similar device. This is because many probe wavelengths of interest fall in the mid-infrared part of the spectrum where direct lasers with sufficient wavelength tuning capability are less common. The efficiency with which OPOs operate is dependent upon the peak power of the pump laser source. Using a pump laser with short pulses having high peak power is normally far more efficient than converting a CW pump laser.

The signal processor 126 combines the measured depolarization states of the scattered light at both wavelengths into different combinations to produce optical input parameters for a discrimination and/or classification algorithm that capture both depolarization and wavelength-dependent backscattering information. As discussed further below, the discrimination and/or classification algorithm may be developed using optical input parameters from samples of known hazardous aerosols, simulants of hazardous aerosols, benign aerosols, background aerosols, and/or modeled aerosol proties.

Demonstration System

The inventors have constructed a system and algorithms according to the invention and demonstrated its usefulness in discriminating anthrax simulant, plague simulant, toxin similant, and virus simulant against a wide range of other dispersed samples.

The system implemented is illustrated in FIG. 2 and has a high degree of functional similarity with the architecture illustrated in FIG. 1, but operates with three wavelengths instead of two. In the implemented system, numeral 201 indicates the transmitter portion of the system and 202 indicates the receiver portion. The transmitter portion incorporates a commercial laser 203 (Continuum model Inlite III) operating at 1064 nm and producing approximately 150 mJ pulse energies at a pulse repetition frequency (PRF) of 20 Hz with a pulse width of 10 ns. The output beam 204 from laser 203 is directed with mirror 205 to beam splitter 206 where a portion of the beam is transmitted to beam splitter 218. The portion of the beam reflected from beam splitter 218 is directed to mirror 223 which directs it to a waveplate assembly 228 contained in motorized assembly 227.

The portion of laser beam 204 that is reflected from beam splitter 206 is transmitted through lenses 209 that form a telescope for mode matching the beam into OPO assembly 211. The OPO assembly 211 comprises mirrors 212 surrounding $LiNbO_3$ crystal 213. When pumped with the 1064 nm beam, part of the 1064 nm energy is converted into a beam 260 at a wavelength of 3389 nm that propagates through lens 214 and is reflected from mirrors 215 and 220 and through optical parametric amplifier (OPA) 221 comprising a crystal of $LiNbO_3$. The third part of 1064 nm beam 204 that is transmitted through beam splitter 218 is reflected from mirror 219 before passing through a mode matching telescope comprising lenses 216. This beam pumps OPA 221. In the process unconverted 1064 nm light 225 is dumped at beam dump 226. The amplification action increases the energy of beam 260, which continues through the crystal and is reflected from mirror 222 and is directed to a second waveplate assembly in motorized assembly 227. The OPA also creates a signal beam 224 at a wavelength of 1551 nm that is reflected from mirror 235 and propagates to a third waveplate assembly in motorized assembly 227. Motorized assembly is controlled by a transmit waveplate actuator 257 via electrical connection 234. The motorized assembly 227 permits rotation of waveplates 228 to cause the polarization state of the three incident laser beams to be altered under computer control. The laser beams 232 emerging from assembly 227 form a set of three transmit laser beams that illuminate a target (not shown) at a suitable distance away from the transmitter. In order to account for variations in power among the three beams sampling beam splitters 229 pick off a small amount of the laser energy and directs the sampled beams 230 to an energy monitor 231 that contains detectors that in turn transmit signals 233 to a computer digitizer card 258 (Acqiris model DC 282). In the demonstrations it was found not to be necessary to use beam combination means to ensure that all beams overlap spatially at the transmitter.

Light 237 scattered from the target particles enters a receiver telescope 238 comprising a large primary mirror 239 and a smaller secondary mirror 240 which causes the received beam to be demagnified and matched in size to the subsequent detectors. At this stage scattered light at all wavelengths overlap in space and time. The overlapped beam is incident on a dichroic optic 241 that reflects the 3389 nm light 242 and directs it to mirror 243, which in turn redirects the light towards receive waveplate assembly 244. The 1064 nm and 1551 nm light transmitted through dichroic 241 continues propagating to a second dichroic optic 245 that reflects the light at 1551 nm as beam 246, which reflects from mirror 247 and is also directed towards receive waveplate assembly 244. The 1064 nm light transmits through both dichroics 241 and 245 and is then incident on waveplate assembly 244. The waveplate assembly is similar in construction to transmit waveplate assembly 227 in that it contains three sets of waveplates whose angular orientation can be controlled remotely by receive waveplate actuator 256 via connection 254 to select a desired polarization state for subsequent detection. The three beams are transmitted through the corresponding waveplates in assembly 244. Each beam then enters a separate receiver 248 that contains four elements. The first element is a polarizer 249 that in conjunction with the corresponding waveplate in assembly 244 permits selection of a polarization state for detection. The second element is a bandpass filter 250 that passes a narrow wavelength range near the corresponding scattered light. This has the effect of reducing noise by rejecting stray background light. The third element is a lens 267 that focuses the received light onto the fourth element, the detector 251 that converts the optical signal to an electrical signal 266. For the demonstration system the detectors used for 1064 and 1551 nm were conventional Si APDs and InGaAs APDs, respectively, while the 3389 nm detectors were MWIR APDs (Raytheon Vision Systems).

The three electrical outputs from the detectors are next passed through a set of amplifiers 252 where the electrical signal is boosted before being sampled using a computer digitizer cards 255 (Acqiris model DC282). The analysis of the signals is completed with custom written LabView software. This enables the computer to extract transmitted and received energy at all three wavelengths. The computer 259 also sends control data 264 to waveplate actuators 257 and 256 and gimbal 267. This flexibility enables the system to independently vary the transmit and receive polarization states and collect data for a large set of polarization state settings in a short time and point the system to a region of interest or provide continuous scanning of the area.

The telescope 238 is primary used for collection of data from relatively distant ranges where the large collection aperture (2" diameter) of primary mirror 239 is beneficial. In the experiments carried out at short ranges the telescope was not necessary and was removed. As a result the received light entered the receiver system along direction 236. A further note is that the transmitter and receiver portions of the system were aligned relative to one another such that the receiver looked at the region of space illuminated by the transmit beam.

The receiver portion 202 provides the computer 256 with measured scattered power at the two polarizations states and the three wavelengths. In the example given above, the three wavelengths were 1551 nm, 1064 nm and 3389 nm, although its is to be understood that other wavelengths may be used. The computer 256 may then combine the measured scattered power at the two polarizations and three wavelengths into different combinations (e.g., based on the combinations in Eq. (3)) to produce optical input parameters for discrimination and/or classification. The optical input parameters provide both depolarization and wavelength-dependent backscattering information. The computer 256 may also receive a signal intensity measurement of the scattered power from the detectors 251.

Figure 2:
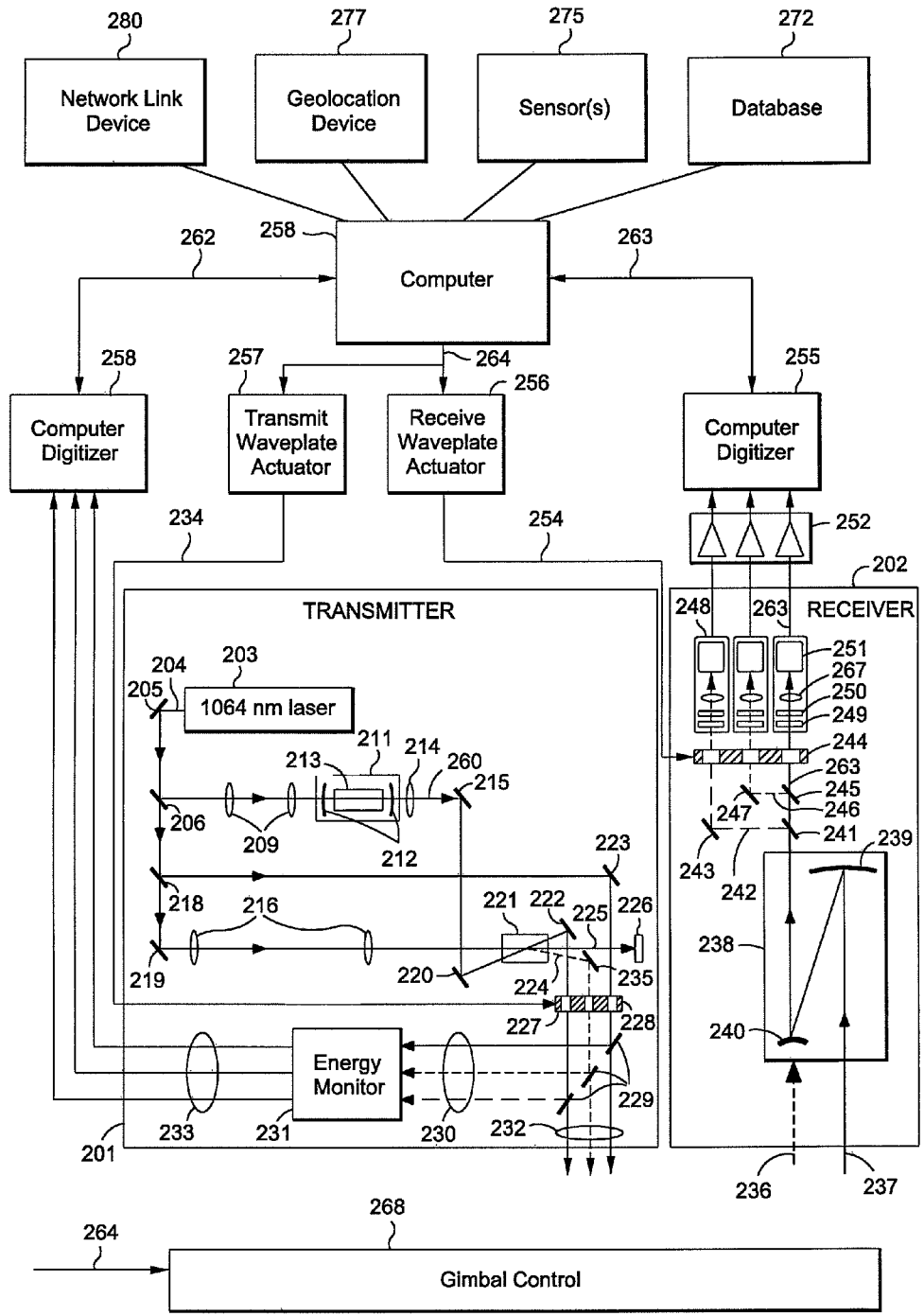
FIG. 2 illustrates a lidar system according to another aspect of the disclosure.

Although three different wavelengths were used in the example in FIG. 2, only two different wavelengths may be used to generate the optical input parameters.

Figure 3:
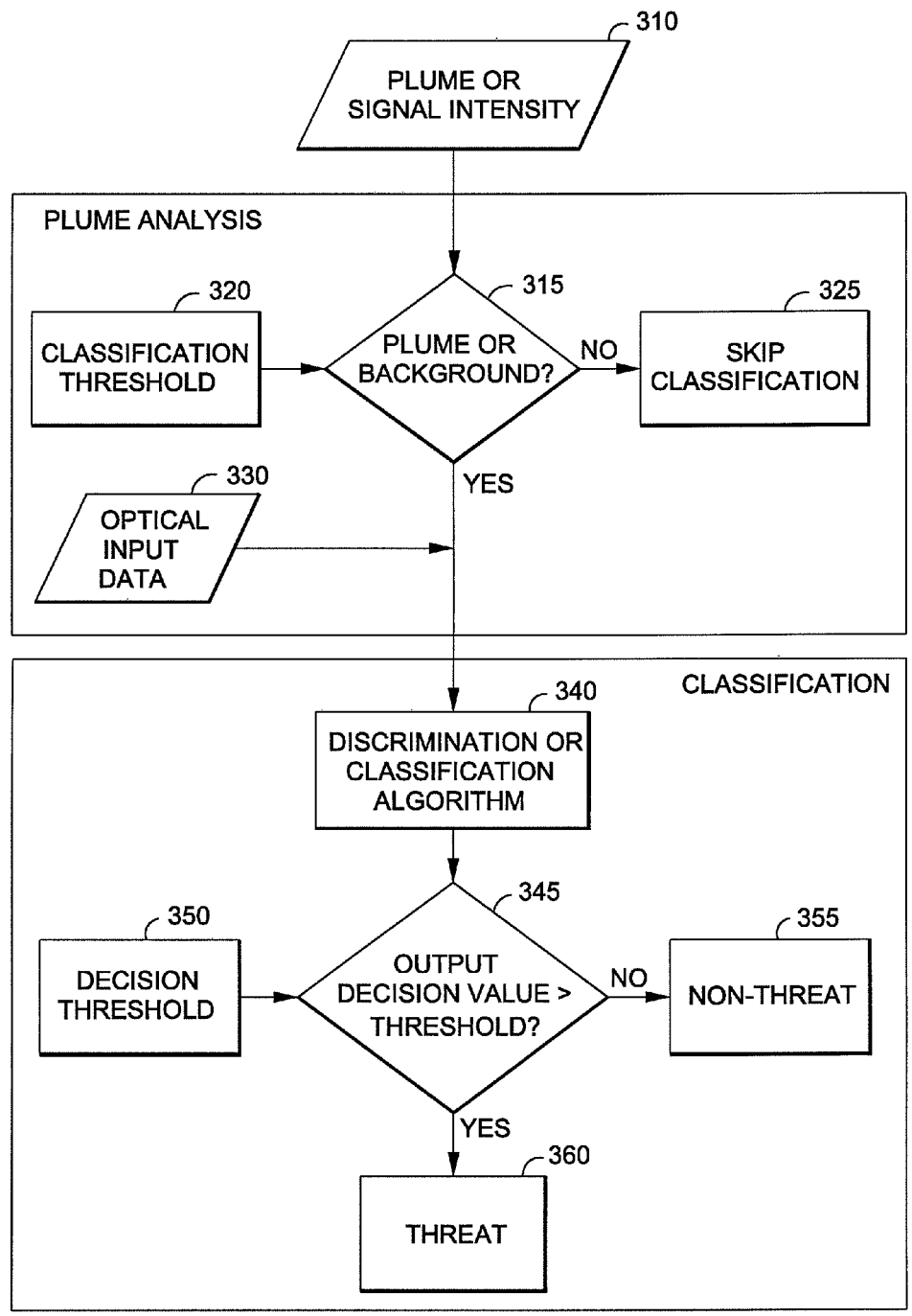
FIG. 3 is a flowchart of a discrimination and/or classification process according to an aspect of the disclosure.

FIG. 3 illustrates a flowchart of a discrimination and/or classification process, which may be performed by the computer 256 in FIG. 2. In step 310, the process receives a signal intensity measurement of the scattered power at the receiver. In step 315, the process compares the signal intensity measurement to a threshold 320 to determine whether the scattered power is from a plume or background noise. For example, if the signal intensity measurement is below the threshold, then the scattered power may be due to background noise rather than a plume that contains a hazardous aerosol. In this case, the process skips discrimination and/or classification in step 325. In step 330, the process receives optical input parameters, which may comprise different combinations of the different polarization states and wavelengths of the measured scattered power. In step 340, the process applies the optical input parameters to a discrimination and/or classification algorithm. For the example of a discrimination algorithm, the discrimination algorithm outputs a decision value indicating a confidence level that a threat classification is correct based on the optical input parameters. In step 345, the process compares the decision value to a decision threshold 350 to determine whether a threat is present. If the decision value is below the decision threshold, then the process determines that there is no threat in step 355. On the other hand, if the decision value is above the decision threshold, then the process declares a threat in step 360. In another aspect, the process may simply declare a threat when the discrimination algorithm determines a threat without assessing the confidence that the threat classification is correct.

Figure 4B:
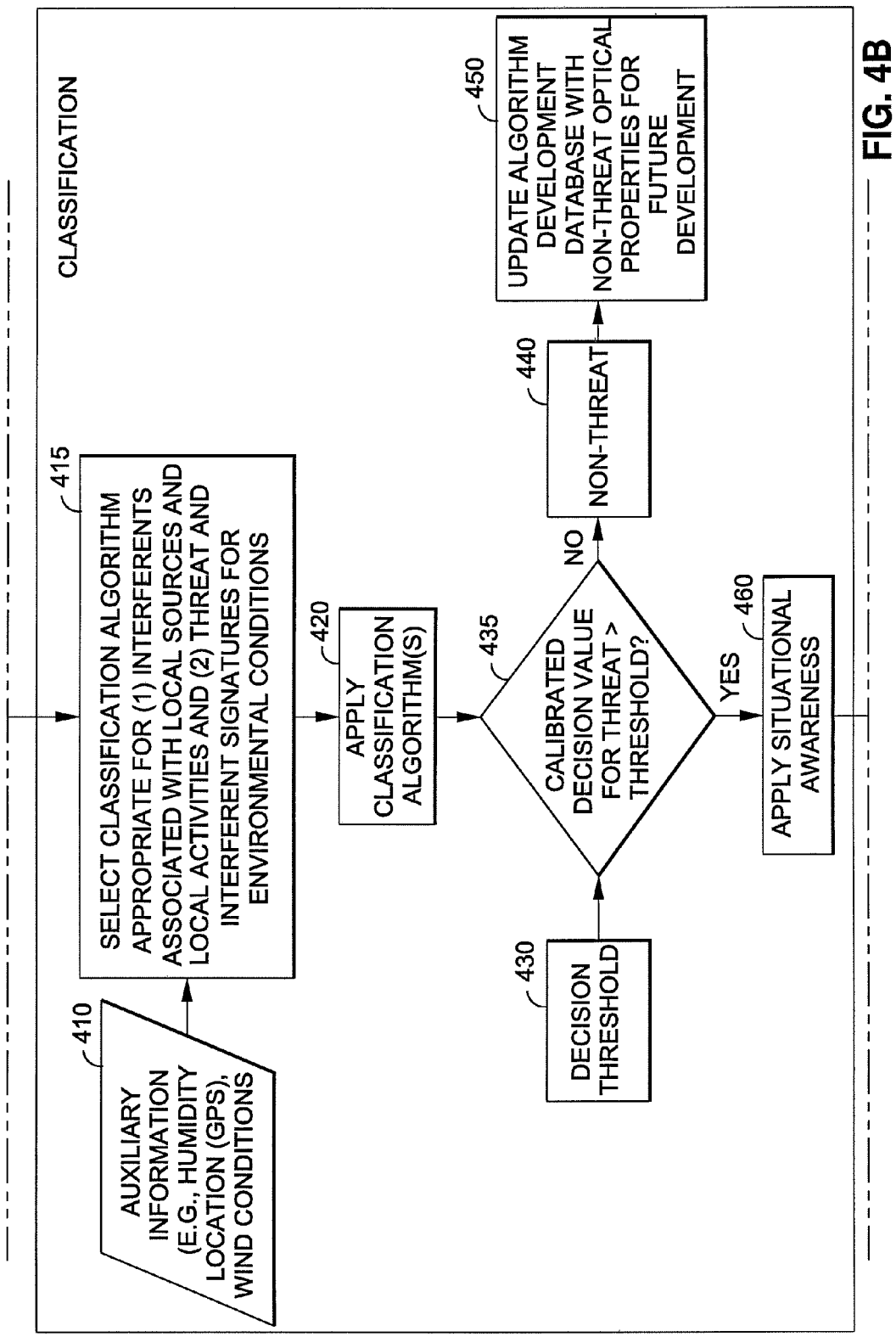
FIG. 4 is a flowchart of a discrimination and/or classification process according to another aspect of the disclosure.
Figure 4C:
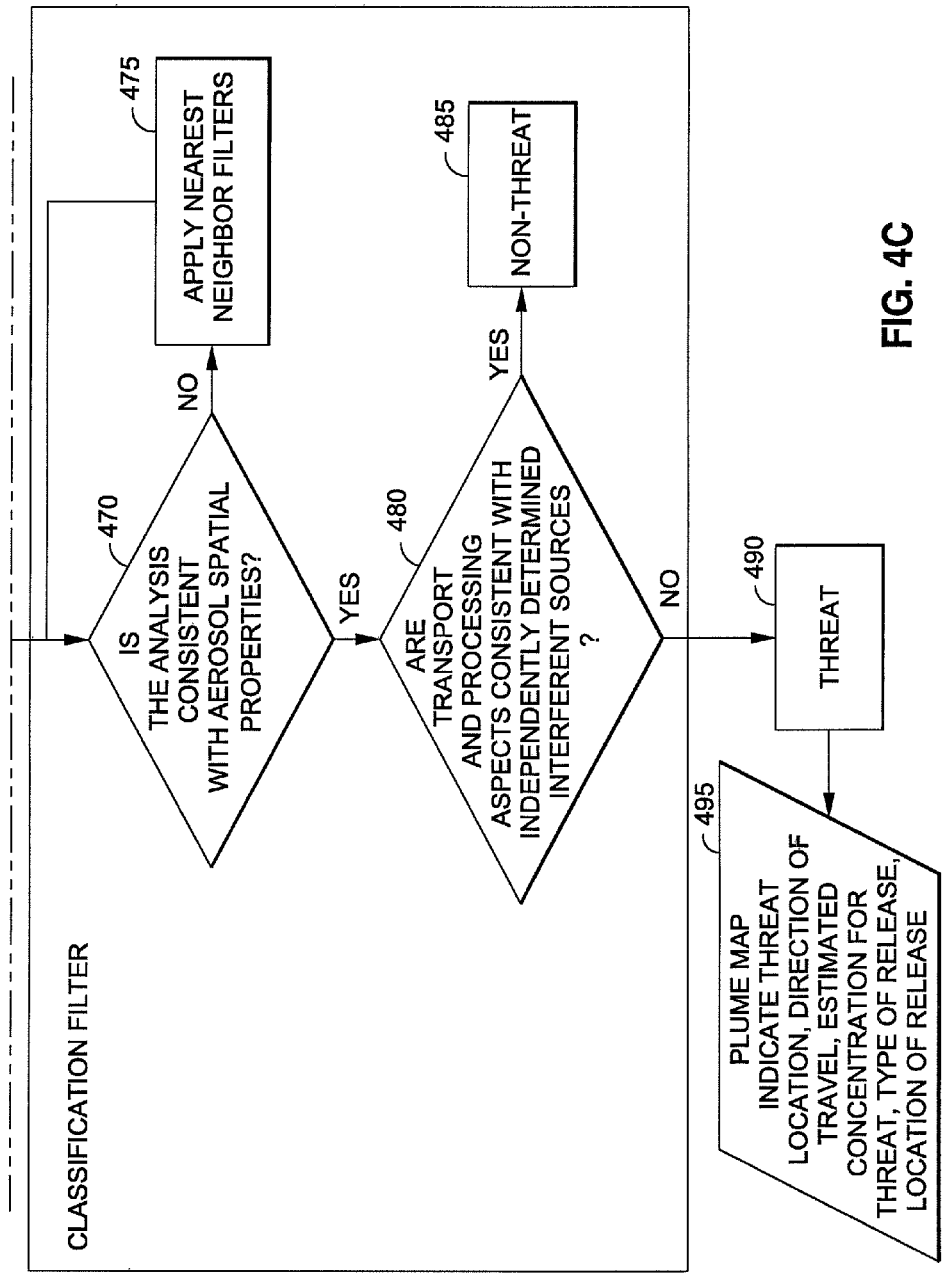

FIG. 4 illustrates a flowchart of a discrimination and/or classification process, which may be performed by the computer 256 in FIG. 2. In steps 310-325, the process determines whether a plume is present similar to the process in FIG. 3. In step 330, the process receives optical input parameters. In step 415, the process determines which discrimination and/or classification algorithm to use from a plurality of algorithms based on auxiliary information, e.g., location of the system (e.g., determined by GPS), humidity, wind conditions, etc. In this aspect, the system in FIG. 2 may comprise a plurality of different algorithms optimized for different interferents and/or conditions stored in database 272. For example, the database 272 may include discrimination and/or classification algorithms optimized for a desert environment (in which the algorithm may be trained with agents of interest and interferents (e.g., dust) under dry conditions), a tropical environment (in which the algorithm may be trained with agents of interest and interferents under high humidity conditions), etc. The system may also comprise one or more sensors 275 (e.g., humidity detector, temperature sensor, etc.) for sensing local conditions and/or a geolocation device 277 (e.g., GPS) for determining the location of the system. The system may also receive the same and/or additional information from a network using a network link device 280 (e.g., transceiver). For example, based on a location fix for the system, the process may select an algorithm optimized for interferents and/or conditions associated with that location. As another example, the system may select an algorithm optimized for low signal-to-noise ratios (SNRs) (in which the algorithm may be trained with data having low SNRs) to detect hazardous materials at low concentrations (corresponding to low signal strengths).

In step 420, the discrimination and/or classification algorithm is applied to the optical input data. For the example of a discrimination algorithm, the discrimination algorithm outputs a decision value indicating a confidence level that a threat classification is correct based on the optical input parameters. In step 435, the process compares the decision value to a decision threshold 430 to determine whether a threat is present. If the decision value is below the decision threshold, then the process declares that there is no threat in step 440 and the optical input parameters for the non-threat may be used to update the algorithm database. On the other hand, if the decision value is above the decision threshold, then the process collects spatial and transportation properties of the suspect threat in step 460. In step 470, the process analyzes the spatial properties of the suspected threat to determine whether they are consistent with the spatial properties of an aerosol. For example, a suspected threat that is confined to a small region may not be consistent with an aerosol plume which disperses in the atmosphere. In this aspect, the system in FIG. 2 may determine the spatial properties of the suspected threat by scanning a large volume (e.g., using the gimbal 268 controlled by the computer 259) and generating a classification map of the scanned volume. If the process determines that the suspected threat is not consistent with the spatial properties of an aerosol plume, then the process may apply nearest neighbor filters in step 475. In step, 480, the process analyzes whether the transportation and processing aspects of the suspected threat are consistent with interferent sources. For example, the process may determine whether the transportation properties of a suspected threat is consistent with transportation properties of exhaust from a truck (an interferent) rather than the dispersion of a hazardous aerosol. If the suspected threat is consistent with the transportation and processing of interferent sources, then the process determines that there is no threat in step 480. On the other hand, if the suspected threat is not consistent, then the process declares a threat in step 490. In this aspect, the system in FIG. 2 may determine the transportation and processing properties of the suspected threat by monitoring changes in the signal strength and/or optical signature of the suspected threat. In step 490, the process may generate a plume map indicating the location of the threat, direction of travel, etc. The plume map may be generated by scanning a large volume (e.g., using a gimbal) and applying the discrimination and/or classification algorithm to the scanned volume.

Development of Discrimination and Classification Algorithms

The development and implementation of discrimination or classification algorithms is based on measurements of optical parameters or modeled optical parameters for biological agents and the option of interferents or materials not of interest for hazardous conditions. Previous measurements or models define the signature for bioaerosol discrimination or classification. The discrimination algorithm can be based a on machine learning algorithm such as support vector machines, neural networks, linear discriminate analysis, decision tree, and stochastic gradient boosting. Due to limitations for available data properly representing the operational implementation, Monte-Carlo based database development or database modification can be implement to define the ground truthed signatures for algorithm development. Examples of possible modification are signal to noise ratio limitation, discrimination of biological species in the presence of benign or non-biological species, or limited data for balanced algorithm training. The developed and implemented algorithm considers relevant aspects associated with benign or non-biological species present, the potential signal intensity of benign or non-biological species, and atmospheric conditions which might alter the optical signatures for biological or non-biological targets.

Figure 5:
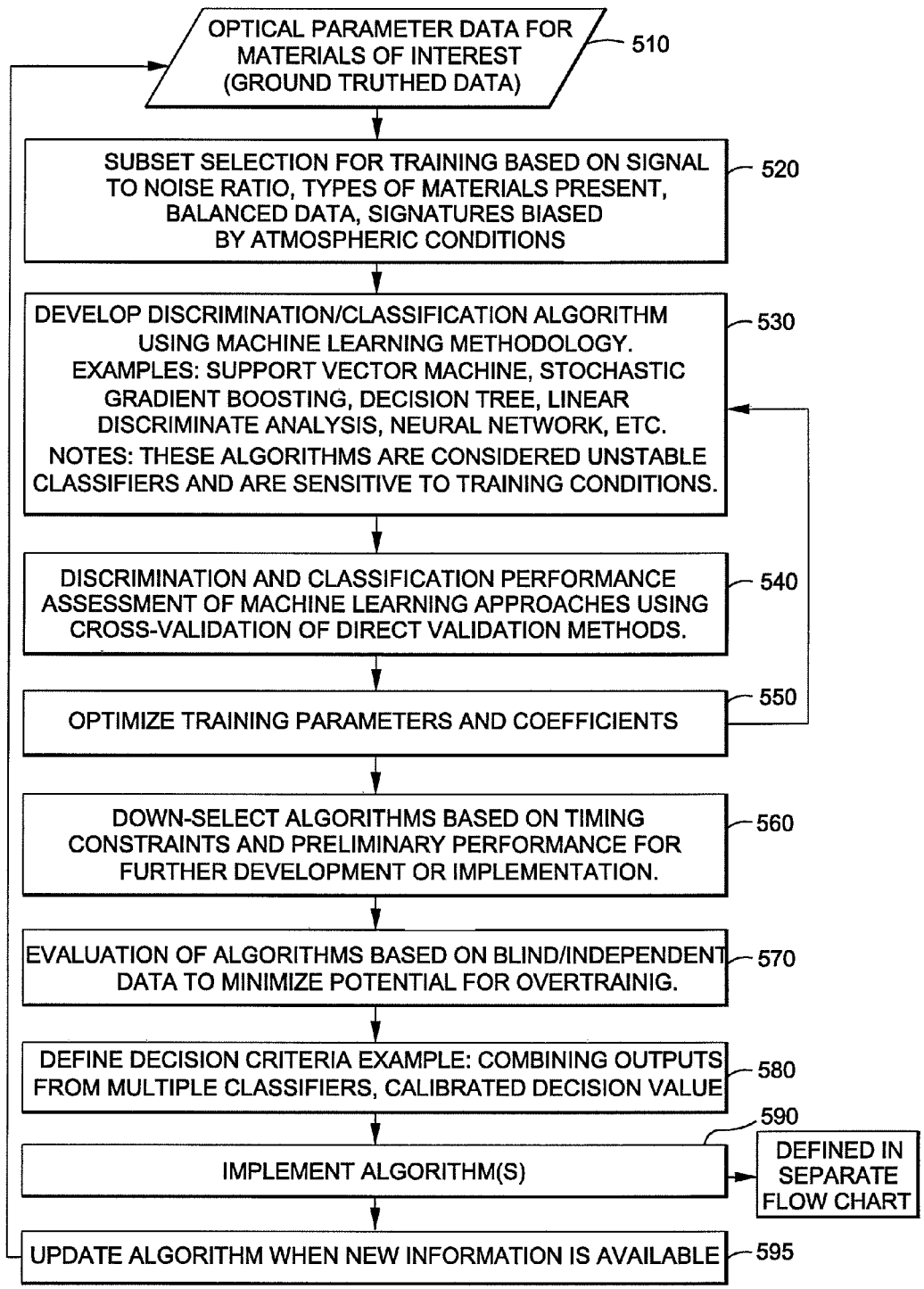
FIG. 5 is a flowchart of a method for developing a discrimination and/or classification algorithm according to an aspect of the disclosure.

FIG. 5 illustrates an example of a method for developing discrimination and/or classification algorithms. In step 510, optical input parameters for known materials are collected to generate a thruthed database. The known materials may include biological agents and interferences under different conditions. In step 520, a subset of the data in the thruthed database is selected to train a discrimination or classification algorithm. The selected data may include input optical parameters for hazardous materials of interest and interferents. For example, if an algorithm is being developed for a desert environment, then the selected interferents may include dust under dry conditions. In step 530, the discrimination and/or classification algorithm is developed using the selected data and a machine learning methodology. For example, a support vector machine may be used to develop the discrimination and/or classification algorithm based on the selected data. In this example, the support vector machine may process the selected data for the hazardous materials of interest and interferents and generate a hyperplane separating the hazardous materials of interest from the interferents. In step 540, a discrimination and/or classification performance assessment of the machine learning process is performed. In step 550, the training parameters and coefficients of the algorithm are optimized. In step 560, developed discrimination and/or classification algorithms may be down selected based on timing constraints and preliminary performance. For example, if an algorithm takes too long to process data for an application requiring fast processing, then the algorithm may not be used. In step 570, the discrimination and/or classification algorithms are evaluated based on blind independent data. For example, a discrimination and/or classification algorithm may be applied to optical input parameters for known materials that were not used to train the algorithm to assess whether the algorithm correctly classifies the materials. In step 580, a decision criteria is defined (e.g., decision threshold) for the discrimination and/or classification algorithm. In step 595, the discrimination and/or classification may be updated when new information becomes available. The steps in FIG. 5 are exemplary only. One or more of the steps may be omitted, and additional steps may be added.

Exemplary Development of Discrimination Algorithms

An example of discrimination algorithm development by the inventors is provided below. In this example, a discrimination algorithm was developed using a support vector machine although it is to be understood that other machine learning methodologies may be used including stochastic gradient boosting, decision tree, etc. Support vector machines may be found, for example, in the Library for Support Vector Machines (LIBSVM) which is available online at http://www.csie.ntu.edu.tw/~cjlin/libsvm.

The example algorithm used a c-svc type SVM model and a radial basis kernel function. Following optimization the parameter values were determined to be C=29.5 and gamma=20.0 with 315 support vectors. The example algorithm was developed using the methodology outlined in FIG. 5.

The algorithm development in this example implementation was based on ground truthed data of agent simulants and benign interferents. Optical signatures were collected with the described instrument during controlled atmospheric releases of relevant materials or surrogates of materials of interest. The contribution from aerosol was eliminated using a background subtraction technique which provided optical signatures of the materials of interest. For this binary classifier implementation ground truthed data for both categories are represented. The discrimination algorithm performance can improve to the theoretical limit by the incorporation of relevant signature variations captured for both categories. The support vector machine implementation was based on maximum margin analysis for separation of the two categories. The boundaries of the two classes are of critical performance. Actual boundaries are defined by optimization technique. A weighted error analysis was used to allow for statistically imbalanced measurements of the two categories.

In this case, randomly sampled data from the data archive for each of the represented subcategories within simulants and interferents are included in the training phase. The training phase was repeated with the various combinations of interest for particular operating conditions. This analysis pertained to interferents composed of the subcategories: smoke (burning hydrocarbons (e.g. diesel, wood), dust (such as that produced from driving on a dirt road or simulated with a blower), pollen (such as that dispersed from pine trees under appropriate wind conditions and during particular growth cycles). The bioaerosol simulants was composed of subcategories: spores (*bacillus anthrasis* and attenuated *bacillus anthrasis*), vegetative bacteria (attenuated *yersinia pestis* and *erwinia herbicola*), toxoids (ricin and ovalbumin), and virus (male-specific coliphage). Each data subset included surrogates for the natural variability by artificial processing, use of various strains, or growth procedures. The data included in this example was collected using the described instrument. The database is composed of 50+ releases composed of the materials listed above.

The support vector machine constants were defined during the training or optimization step using the training data. Therefore the ground truthed data that enters the machine learning algorithm is evaluated for artifacts, data quality, and accuracy of ground truth information. Training and cross-validation used 20% of database including the above listed materials. The cost function was set to optimize the algorithm toward the and detection of surrogate in the presence of interferents and reduction of false alarms due to the statistical dominance of interferent or benign plumes compared to biological agents. In this example, the cost for misclassification of a false positive was set to 1 where the cost of a false negative was varied from 1 to 0.5.

Raw training results are provided in Table 1 below. True negatives indicate proper discrimination of non-hazardous conditions. True positives indicated proper discrimination of simulated hazardous conditions. False positives indicate prediction of hazardous conditions when benign conditions are present. False negatives indicate prediction of non-hazardous conditions when hazardous conditions are present. The raw training results are based on 1 second measurements and values are reported as a fraction of non-hazardous conditions in the top row and hazardous conditions in the bottom row.

TABLE 1

| Training | | Predicted Category | |
|---|---|---|---|
| | | F | P |
| Actual Category | F | 0.989 | 0.011 |
| | P | 0.002 | 0.998 |

Cross-validation results are provided in Table 2 below. These results were determined following the setting of the SVM constants and support vectors. The misclassification is slightly high in the case of validation than training.

TABLE 2

| Validation | | Predicted Category | |
|---|---|---|---|
| | | F | P |
| Actual Category | F | 0.978 | 0.022 |
| | P | 0.003 | 0.997 |

Figure 6:
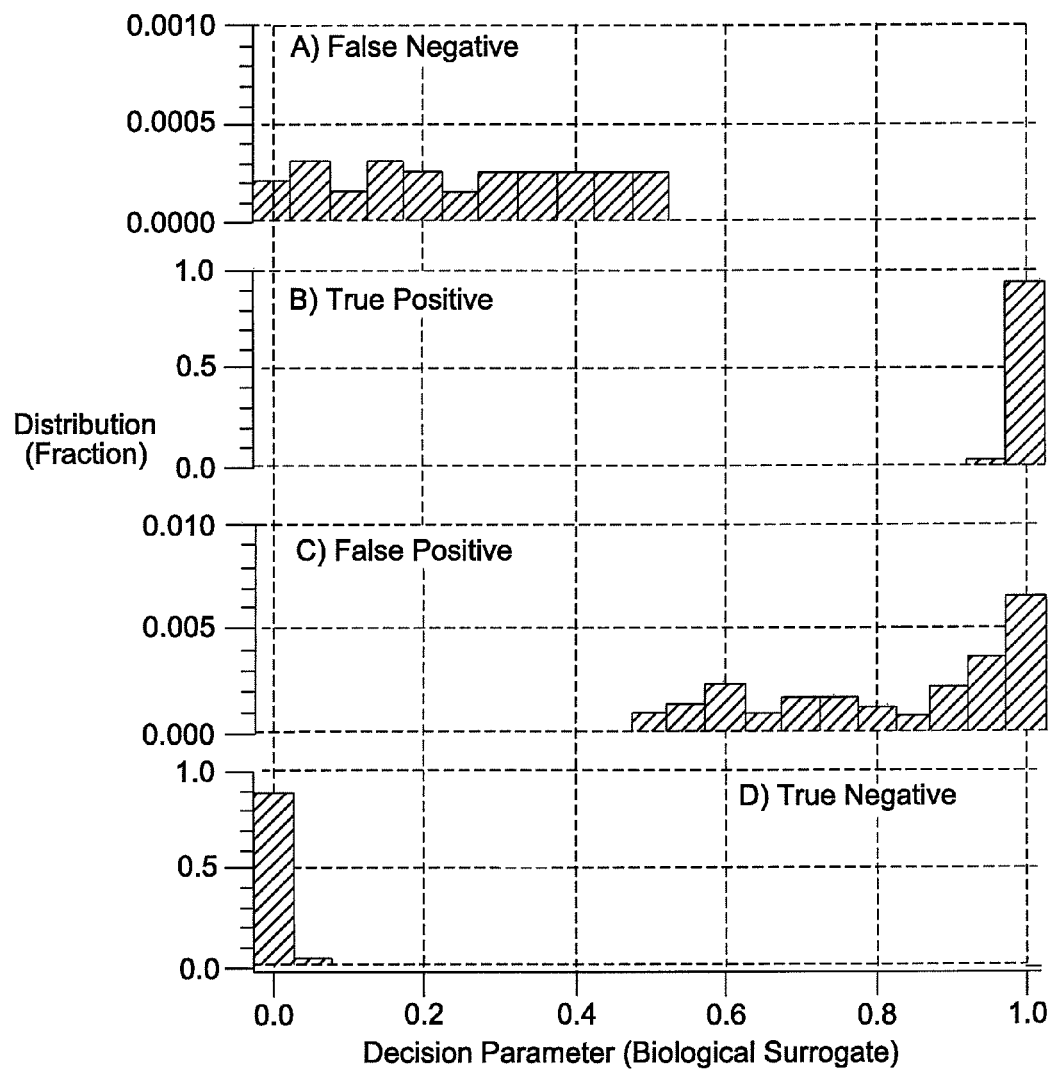
FIG. 6 shows an example of distribution of a decision parameter for biological surrogates according to an aspect of the disclosure.

The distribution of decision parameters associated with hazardous conditions for the case of false negatives, true positives, false positives, and true negatives are shown in FIG. 6. A value of 1 indicated high confidence in hazardous conditions. A value of 0 indicated high confidence in non-hazardous conditions. The decision parameter is based on distance from the separation hyperplane.

The reality of field operation provides sufficient opportunity for occasional measurement errors. The analysis of hazardous aerosol detection and discrimination technology needs to evaluate classification error due to measurement error from limitations due to non-separable optical properties for particular hazardous and non-hazardous aerosol. In this example this was completed by applying a nearest neighbor filter which required consistent prediction of hazardous conditions over a ten second interval prior to signaling a hazardous condition was observed. Misclassification results following the described filter are shown in Table 3 below. There is significant improvement between the results shown in Table 2 and Table 3 as a result of filtering. These improvements are related to measurement precision or measurement error within the evaluation database.

TABLE 3

| Filtered | | Predicted Category | |
|---|---|---|---|
| | | F | P |
| Actual Category | F | 0.998 | 0.002 |
| | P | 0.000 | 1.000 |

Figure 7:
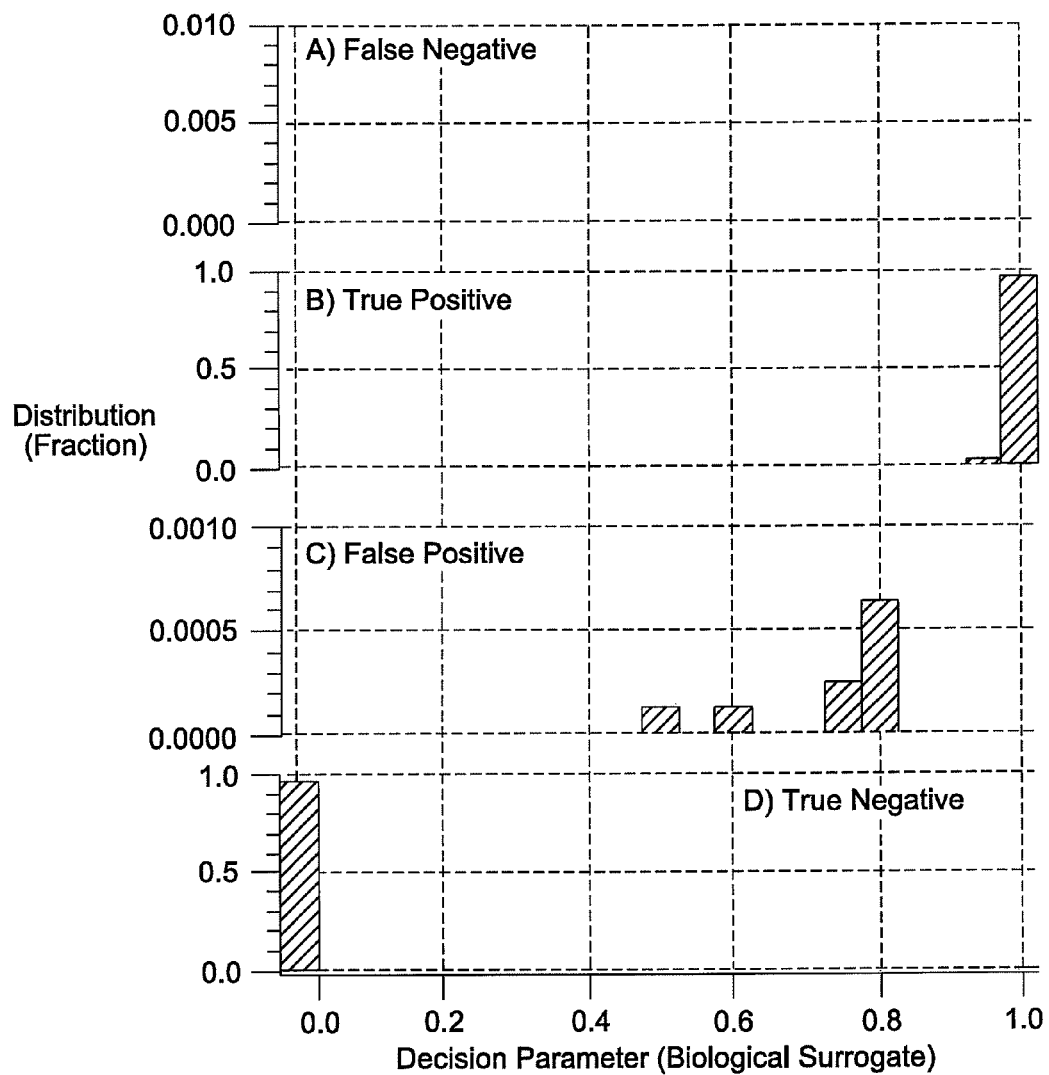
FIG. 7 shows an example of distribution of a decision parameter for geological surrogates following nearest neighbor filtering according to an aspect of the disclosure.

The distribution of decision parameter with respect to hazardous conditions following the nearest neighbor filter is shown in FIG. 7. The results are consistent with the data shown in Table 3 indicating significant improvement from the raw results.

This last filtering step is representative of the classification filtering designed for real-time algorithm implementation and the improved predictive performance. The results can further be improved by applying a decision parameter criteria or threshold prior to predicting a hazardous condition. In this example a decision threshold of 0.85 leads for perfect performance regarding hazardous and non-hazardous conditions of the described hardware and algorithm implementation. When a decision threshold is applied in this fashion it influences the type of mixtures of hazardous and non-hazardous aerosol that can be properly identified as a hazardous condition.

In this discussion, the words simulant, surrogate, and hazardous condition to refer to testing situation compared to true application of system which will be the detection and discrimination of bioaerosol agent, bioaerosol threats, and hazardous aerosol. The example given above is for illustrative purposes only. Other discrimination and/or classification algorithms may be implemented using the same or different development methodologies.

Development of Anomaly Discrimination Algorithm

The development of anomaly discrimination algorithm based on deviations from typical behavior is based on well characterized optical signatures based on the polarization and wavelength dependent measurements incorporated in intensive and/or extensive properties. The anomaly discrimination algorithm can be previously developed and adaptive based on continuously updated with measurements were threat and hazardous conditions are monitored. In this case, predicted hazardous conditions are based on a exceeding a predetermined or adaptive threshold associated with deviation of the intensive or extensive properties.

Selection of Implemented Algorithms

Selection of an algorithm can be optimized to increase accuracy associated with minimization of false alarms and positive alarm. Some particulate species signatures with are altered by relative humidity and physical state. Local measurements or forecast of temperature and humidity can be used to influence the implemented algorithm. The input parameters cannot be scaled without know the identity of the target species. Therefore, it is advantageous to select the algorithm based on environmental condition. Selection based local sources of naturally occurring particles and activities with expected sources or direct measurements at operation site. Seasonal variations related to interferents can also be incorporated to optimize decision confidence (e.g. pollen conditions). Continuous or scheduled updates associated with detected interferents can further improve decision confidence.

Alternative Embodiments

Numerous alternative and beneficial embodiments of the invention are possible. One alternative embodiment uses a tunable or multi-wavelength source to produce probe light over a predetermined spectral range to collect data at a multiplicity of wavelengths. The construction of a tunable system of this nature is not dependent on a particular type of light source, but one exemplary type is an electrically tunable Cr:ZnSe solid-state laser pumping an OPO as described by A. Zakel et al. in "*High-brightness rapidly-tunable Cr: ZnSe lasers*", 20$^{th}$ Anniversary Meeting Advanced Solid-State Photonics, Feb. 6-9, 2005, Vienna. Rapid electrical tuning of a Q-switched Cr:ZnSe laser has been demonstrated over a spectral range of 2.1-2.8 μm and use of this laser to pump an OPO (for example $ZnGeP_2$ or CdSe) can provide a pulsed source covering the mid- to long-wave infrared spectrum from approximately 2-14 μm.

From an operational and low cost standpoint is may be beneficial to construct simple systems that use only two wavelengths and use fixed transmit and receive polarization controllers, for example transmitting one linear polarization state and receiving two linear polarization states. Polarization states useful in a particular application are determined through calibration experiments prior to construction of the system. However a more complicated system that transmits and collects four polarization states and calculates the entire Mueller matrix of the material may provide greater discrimination ability.

Although the system has been described primarily in terms of usefulness to making measurement with scalability to long ranges, it is equally clear that the method is also useful for short-range measurements, for example in scanning mail and parcels at sorting stations for the presence of undesired airborne materials. In such short-range cases it is generally not required that the light source produce highly energetic pulses. To reduce complexity and cost diode-lasers, LEDs, and filtered broadband emitters may be advantageously utilized.

Yet one more alternative embodiment would use a wavelength switchable source to output several wavelengths and/or polarizations for sequential measurements. Implementing such a system may enable the use of as few as a single broadband detection channel provided that the receiver incorporates means as discussed to switch between receive polarization states. A system using two detection channels could be constructed to receive two polarization states simultaneously and wavelength switching used to collect data at the plurality of wavelengths.

The demonstrated system can be improved upon in a number of areas. Use of a telescope as noted with reference to FIG. 2 will significantly extend the range at which detection can take place. Optimization of detectors to minimize noise would also be beneficial, for example utilizing photon-counting detectors. One possibility is the use of HgCdTe APD detectors that have the potential for very low noise detection over a very wide spectral range from <1 µm to >10 Scaling of the results obtained indicate that systems can be built that permit operation at stand-off ranges exceeding 1 km. For operational use a scanning system is also beneficial to enable coverage of a large volume in space. Such a system can also easily be used in conjunction with geolocation (e.g. GPS) and direction sensors to identify the absolute or relative location of detected species. When a pulsed light source is used the time delay between transmission and reception of the scattered light can be used to determine range to the scatterers, which, in conjunction with the aforementioned GPS and/or direction sensors can be used to determine the 3 dimensional coordinates of the scatterers. A system used in this manner can easily report the presence and/or location of species to emergency response teams or other designated responders.

The objective of the demonstration system discussed with reference to FIG. 2 was to demonstrate discrimination of BG against other materials, but a system using the described method can be used to detect a wider range of materials provided that the materials are characterized spectrally with respect to depolarization properties.

Throughout this disclosure the term "light" has been used to describe the radiation emitted and detected. It is noted that this term should be interpreted in broad terms, covering the entire electromagnetic spectral range, rather than being used to denote a specific range of radiation frequencies.

A further alternative use of the system is in conjunction with a second lidar system, where the second system is capable of detecting the presence of aerosols or other emission plumes over a large area or volume through rapid scanning, and the disclosed invention is subsequently utilized to probe the detected area/volume for the presence of specific chemical or biological agents of interest. This arrangement may be particularly useful if the area/volume search rate of the second system is greater then that of the invention.

Alternatives associated with algorithm implementation include limiting the use of auxiliary data to select the optimized discrimination and/or classification algorithm. Auxiliary data can include meteorological data as described previously or inputs for other sensors such as biological or aerosol detectors part of a system network. Another alternative is running multiple parallel discrimination and/or classification algorithms or algorithms in series to improve the predictive performance.

The benefits of the presented invention enable a number of applications that include, but are not limited to: remote detection and characterization of aerosols, mapping distributions of dispersed airborne material, determination of material direction of travel, early warning of unintended or intended release of biological agent, and estimated time to intercept of biological agent. Although the invention has been described and illustrated with a certain degree of particularity, it is understood that the present disclosure has been made only by way of example, and that numerous changes in the combination and arrangement of parts and algorithms can be resorted to by those skilled in the art without departing from the spirit and scope of the invention, as hereinafter claimed.

Those of skill in the art would appreciate that the various illustrative blocks, modules, elements, components, methods, and algorithms described herein may be implemented as electronic hardware, computer software, or combinations of both. Furthermore, these may be partitioned differently than what is described. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." All structural and functional equivalents to the elements of the various aspects described throughout this invention that are known or later come to be known to those of ordinary skill in the art are expressly incorporated herein by reference and are intended to be encompassed by the claims. Moreover, nothing disclosed herein is intended to be dedicated to the public regardless of whether such invention is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A detection system, comprising:
    a transmitter configured to transmit electromagnetic energy at two or more wavelengths, wherein the electromagnetic energy has a selected polarization state;
    a receiver configured to receive scattered electromagnetic energy that has been scattered by a material illuminated by the transmitted electromagnetic energy, and measure the received polarization states at the two or more wavelengths and total backscatter intensity at the two or more wavelengths;
    a processor configured to combine the measured polarization states at the two or more wavelengths and the total backscatter intensity at the two or more wavelengths into a plurality of different combinations to obtain input parameters, wherein each combination comprises the power of one of the polarization states at one of the wavelengths divided by the power of the total backscatter intensity across the two or more wavelengths, and to classify the material illuminated by the transmitted electromagnetic energy based on the input parameters.

2. The detection system of claim 1, wherein the processor is configured to classify the material as a threat or a non-threat.

3. The detection system of claim 1, wherein the processor is configured to classify the material as a biological or non-biological material.

4. The detection system of claim 1, wherein the input parameters include both depolarization and wavelength-dependent backscattering information of the material illuminated by the transmitted electromagnetic energy.

5. The detection system of claim 1, wherein the transmitter is configured to alter the selected polarization state based on a control signal.

6. The detection system of claim 1, wherein the transmitter is configured to alter the two or more wavelengths of the transmitted electromagnetic energy based on a control signal.

7. The detection system of claim 1, wherein the transmitter is configured to transmit electromagnetic energy at a first and a second wavelengths of the two or more wavelengths simultaneously.

8. The detection system of claim 1, wherein the transmitter is configured to pulse the transmitted electromagnetic energy.

9. The detection system of claim 1, wherein the transmitter is configured to transmit the electromagnetic energy at three or more wavelengths.

10. The detection system of claim 1, wherein the transmitter is configured to transmit the electromagnetic energy in a continuous wave.

11. The detection system of claim 1, wherein the processor is configured to classify the material to a species of a hazardous material.

12. The detection system of claim 1, wherein the transmitter comprises a device selected from the group consisting of: lasers, non-linear optical sources, light emitting diodes, and filtered broadband sources.

13. The detection system of claim 1, further comprising a telescope optically coupled to the receiver and configured to gather scattered electromagnetic energy.

14. The detection system of claim 1, further comprising a spatial scanning system configured to move the transmitter and receiver to scan a volume.

15. The detection system of claim 14, wherein the processor is configured to determine spatial properties of the material using the spatial scanning system, and to determine whether the spatial properties of the material are consistent with spatial properties of a hazardous aerosol of interest.

16. The detection system of claim 14, wherein the processor is configured to determine transportation properties of the material using the spatial scanning system, and to determine whether the transportation properties are consistent with dispersion of a hazardous aerosol of interest.

17. The detection system of claim 1, further comprising a database including a plurality of classification algorithms, and wherein the processor is configured to select one of the plurality of classification algorithms to classify the material.

18. The detection system of claim 17, wherein one or more of the classification algorithms is configured to classify a material as a threat or a non-threat.

19. The detection system of claim 17, further comprising a location device, and wherein the processor is configured to select one of the classification algorithms based on a location fix from the location device.

20. The detection system of claim 17, further comprising one of more sensors, and wherein the processor is configured to select one of the plurality of classification algorithms based on a sensor reading from the one or more sensors.

21. The detection system of claim 20, wherein the one or more sensors are selected from a group consisting of: humidity sensor, temperature sensor and wind sensor.

22. The detection system of claim 1, wherein the transmitter is configured to transmit the electromagnetic energy in pulses.

23. The detection system of claim 1, wherein the selected polarization state is linear, circular or a combination of both.

24. A method of detection, comprising:
    transmitting electromagnetic energy at two or more wavelengths, wherein the electromagnetic energy has a selected polarization state;
    receiving scattered electromagnetic energy that has been scattered by a material illuminated by the transmitted electromagnetic energy;
    measuring the received polarization states at the two or more wavelengths and total backscatter intensity at the two or more wavelengths;
    combining the measured polarization states at the two or more wavelengths and the total backscatter intensity at the two or more wavelengths into a plurality of different combinations to obtain input parameters, wherein each combination comprises the power of one of the polarization states at one of the wavelengths divided by the power of the total backscatter intensity across the two or more wavelengths; and
    classifying the material illuminated by the transmitted electromagnetic energy based on the input parameters.

25. The method of claim 24, wherein the classifying step comprises classifying the material as a threat or a non-threat.

26. The method of claim 24, wherein the classifying step comprises classifying the material as a biological or non-biological material.

27. The method of claim 24, wherein the input parameters include both depolarization and wavelength-dependent backscattering information of the material illuminated by the transmitted electromagnetic energy.

28. The method of claim 24, further comprising altering the selected polarization state based on a control signal.

29. The method of claim 24, further comprising altering the two or more wavelengths of the transmitted electromagnetic energy based on a control signal.

30. The method of claim 24, further comprising transmitting the electromagnetic energy at a first and a second wavelengths of the two or more wavelengths simultaneously.

31. The method of claim 24, further comprising pulsing the transmitted electromagnetic energy.

32. The method of claim 24, further comprising transmitting the electromagnetic energy at three or more wavelengths.

33. The method of claim 24, further comprising transmitting the electromagnetic energy in a continuous wave.

34. The method of claim 24, wherein the classifying step comprises classifying the material to a species of a hazardous material.

35. The method of claim 24, further comprising:
determining transportation properties of the material; and
determining whether the transportation properties of the material are consistent with dispersion of a hazardous aerosol of interest.

36. The method of claim 24, further comprising selecting a classification algorithm from a plurality of classification algorithms to perform the classification step.

37. The method of claim 36, wherein one or more of the plurality of classification algorithms is configured to classify a material as a threat or non-threat.

38. The method of claim 24, further comprising:
determining spatial properties of the material; and
determining whether the spatial properties of the material are consistent with spatial properties of a hazardous aerosol of interest.

39. The method of claim 36, wherein the selecting step comprises selecting a classification algorithm based on a location fix.

40. The method of claim 38, wherein the selecting step comprises selecting a classification algorithm based on a sensor reading.

41. The method of claim 40, wherein the sensor reading comprises a humidity reading, temperature reading or a wind reading.

42. The method of claim 38, wherein the selecting step comprises selecting a classification algorithm based on a signal-to-noise ratio.

* * * * *